United States Patent [19]

Westfechtel et al.

[11] Patent Number: 5,416,239

[45] Date of Patent: May 16, 1995

[54] PROCESS FOR THE PRODUCTION OF FATTY KETONES

[75] Inventors: Alfred Westfechtel, Hilden; Christoph Breucker, Haan; Bernhard Gutsche, Hilden; Lutz Jeromin, Hilden; Horst Eierdanz, Hilden; Horst Baumann, Leichlingen; Karl-Heinz Schmid, Mettmann; Werner Nonnenkamp, Linz, all of Germany

[73] Assignee: Henkel Kommanditgesellschaft auf Aktien, Duesseldorf, Germany

[21] Appl. No.: 167,926

[22] PCT Filed: Jun. 17, 1992

[86] PCT No.: PCT/EP92/01373

§ 371 Date: Feb. 17, 1994

§ 102(e) Date: Feb. 17, 1994

[87] PCT Pub. No.: WO93/00320

PCT Pub. Date: Jan. 7, 1993

[30] Foreign Application Priority Data

Jun. 26, 1991 [DE] Germany .................. 41 21 117.0

[51] Int. Cl.⁶ ............................................. C07C 45/45
[52] U.S. Cl. ......................................................... 568/397
[58] Field of Search .......................................... 568/397

[56] References Cited

U.S. PATENT DOCUMENTS 3,391,191  7/1968  Velde ................... 260/595
5,001,273  3/1991  Kleine-Homann ................... 568/397

OTHER PUBLICATIONS

Org. Synth., vol. 33, S.854 ff.
J. Soc.Chem. Ind. 66, 402 (1947).
Chem. Ing.-Tech. 62, 416 u. 512 (1990).
Houben–Weyl, Methoden der Organischen Chemie, Thieme-Verlag, Stuttgart, Bd. 7/2a, S.622 ff.

*Primary Examiner*—James H. Reamer
*Attorney, Agent, or Firm*—Ernest G. Szoke; Wayne C. Jaeschke; Henry E. Millson, Jr.

[57] ABSTRACT

A process for the production of fatty ketones by pyrolysis of fatty acid magnesium salts wherein fatty acids corresponding to formula (I):

$$R^1COOH \qquad (I)$$

in which $R^1CO$ is an aliphatic acyl radical containing 12 to 22 carbon atoms and 0, 1, 2 or 3 double bonds, are heated to temperatures of 320° to 360° C. in the presence of magnesium oxide and the fatty ketones formed are distilled off from the reaction mixture under reduced pressure.

6 Claims, No Drawings

PROCESS FOR THE PRODUCTION OF FATTY KETONES

BACKGROUND OF THE INVENTION

1. Field of the Invention

This invention relates to a process for the production of fatty ketones by pyrolysis of fatty acid magnesium salts.

2. Statement of Related Art

Long-chain symmetric and asymmetric ketones based on fatty acids, so-called "fatty ketones" are used either directly or after sulfonation or quaternization as additives for fabric softeners, hair shampoos, corrosion inhibitors or flotation aids (*Chem. Ing.-Tech.* 62, 416 and 512 (1990).

The production of fatty ketones by pyrolysis of fatty acid salts in the presence of catalytic quantities of calcium, iron or manganese salts has been known since 1855 and is covered by extensive literature (*Houben-Weyl, Methoden der Organischen Chemie,* Thieme-Verlag, Stuttgart, Vol. 7/2a, pages 622 et seq.).

Recently, magnesium oxide has been successfully used as the catalyst. Thus, a laboratory process for the production of stearone, in which 1 mole of stearic acid and 0.5 mole of magnesium oxide are reacted at 340° C., is described, for example, in *Org. Synth.,* Vol. 33, pages 854 et seq. For working up, the crude product has first to be washed with sulfuric acid, water and sodium hydrogen carbonate solution, the pure stearone only being obtained after two crystallizations. In addition, it is recommended that foam formed during the reaction be either mechanically destroyed or controlled by antifoam agents. In overall terms, a process such as this is unsuitable for industrial application on account of the high outlay on equipment for working up.

A process for the production of fatty ketones by pyrolysis of magnesium salts of fatty acids is also known from *J. Soc. Chem. Ind.* 66, 402 (1947). To solve the foam problems, it is proposed in this reference initially to introduce the fatty acid in far less than the equivalent quantity relative to the magnesium oxide, to heat the reaction mixture and then continuously to introduce the remaining fatty acid. Although foam problems can be minimized in this way, they cannot be eliminated altogether so that part of the fatty acid is still discharged and is thus lost in the absence of additional measures. Another disadvantage of the process is that the magnesium salt has to be separated by filtration, sedimentation or treatment with mineral acids after the reaction and, accordingly, cannot be quantitatively removed from the products.

Accordingly, the problem addressed by the present invention was to provide a new process for the production of fatty ketones which would not have any of the disadvantages described above.

DESCRIPTION OF THE INVENTION

The present invention relates to a process for the production of fatty ketones by pyrolysis of fatty acid magnesium salts, characterized in that fatty acids corresponding to formula (I):

in which $R^1CO$ is an aliphatic acyl radical containing 12 to 22 carbon atoms and 0, 1, 2 or 3 double bonds, are heated to temperatures of 320° to 360° C. in the presence of magnesium oxide and the fatty ketones formed are distilled off from the reaction mixture under reduced pressure.

Although the production of fatty ketones by pyrolysis of fatty acid magnesium salts has been known for some time, it has only now surprisingly been found that the foaming and associated problems can be suppressed in the production process if the fatty ketones are distilled off from the reaction mixture under reduced pressure at the reaction temperature. In this way, losses of starting material are avoided and products with only a minimal magnesium content in relation to the prior art are obtained. By virtue of the fact that the fatty ketones have only a short residence time in the hot reaction zone as a result of distillation, so that they are not seriously exposed to high temperatures, light-colored products are surprisingly obtained, the chromophoric groups remaining in the bottom product of the distillation process. The present invention also includes the observation that the bottom product accumulating during the reaction can be directly reacted with fatty acid again so that the process can be carried out semi-continuously. Further advantages of the process lie in the fact that the process can be carried out under isothermal conditions and in the short batch times. There is no need for complete pyrolysis because the magnesium soaps formed as intermediate products, which are not pyrolyzed, remain in the bottom product.

Fatty acids which may be used as starting materials in accordance with the invention correspond to formula (I):

in which $R^1CO$ is an aliphatic acyl radical containing 12 to 22 carbon atoms and 0, 1, 2 or 3 double bonds. Typical examples are lauric acid, myristic acid, palmitic acid, palmitoleic acid, stearic acid, oleic acid, elaidic acid, petroselic acid, linoleic acid, linolenic acid, arachic acid, gadoleic acid, behenic acid or erucic acid. Fatty acids corresponding to formula (I), in which $R^1CO$ is a $C_{16-18}$ acyl radical, more particularly a stearyl radical, are preferably used.

As usual in oleochemistry, the fatty acids may also be used in the form of the technical cuts obtained, for example, by the pressure hydrolysis of fats and oils, for example palm oil, palm kernel oil, coconut oil, rapeseed oil, sunflower oil, coriander oil, cotton oil, peanut oil, olive oil, linseed oil, soybean oil or beef tallow.

The pyrolysis may be carried out at temperatures in the range from 290° to 450° C. Temperatures in the range from 320° to 345° C. have proved to be optimal in regard to a high yield and light-colored products.

The fatty acids and the magnesium oxide may be used in a molar ratio of 1:0.5 to 1:10 and preferably in a molar ratio of 1:0.6 to 1:1. In one preferred embodiment of the process, the magnesium oxide is initially contacted with 5 to 20% by weight of the total quantity of fatty acid, the mixture is heated to the reaction temperature and the remaining quantity of fatty acid is subsequently introduced.

The pure products are recovered from the reaction mixture without further purification by distilling off the fatty ketones formed during the pyrolysis at the reaction temperature and under a reduced pressure of 1 to 50 mbar.

In another preferred embodiment of the invention, the bottom product accumulating during the distillation process is reintroduced into the reaction in a quantity corresponding to the fatty acid consumed, so that the reaction can be carried out semi-continuously.

Industrial Applications

The fatty ketones obtained are light in color without bleaching and have extremely small magnesium contents. They are suitable as additives for fabric softeners, hair shampoos, corrosion inhibitors or flotation aids in which they may be present in quantities of 0.1 to 25% by weight and preferably in quantities of 1 to 10% by weight, based on the particular preparation. In addition, they may be converted into surface-active substances by sulfonation or quaternization.

The following Examples are intended to illustrate the invention without limiting it in any way.

EXAMPLES

Example 1

Production of 18-pentatriacontanone (stearone).

A mixture of 57 g (0.2 mole) of octadecanoic acid and 81 g (2.0 mole) of magnesium oxide was heated to 340° C. in a three-necked flask equipped with a dropping funnel and distillation bridge. After a reaction time of 60 minutes, another 1026 g (3.6 mole) of octadecanoic acid were added dropwise, $CO_2$ and water being eliminated. The reaction mixture was kept at the above temperature for another 60 minutes, after which the reaction product was distilled off from the bottom product under reduced pressure (p=10 mbar). The yield of stearone (distillate) was 70% of the theoretical; the Mg content was <50 ppm.

Example 2

The sump product of Example 1 under a vacuum was further processed. The vacuum was first broken by introduction of nitrogen, after which another 912 g (3.2 mole) of stearic acid were added to the bottom product at a temperature of 340° C. The reaction mixture was further processed as in Example 1. The yield of stearone again amounted to 70% of the theoretical.

The cycle was repeated 10 times. The yield per cycle amounted to a constant approximately 70% of the theoretical.

We claim:

1. A process for the semi-continuous production of fatty ketones by pyrolysis of fatty acid magnesium salts comprising the steps of A) reacting at least one fatty acid of formula I $$R^1COOH \qquad (I)$$

in which $R^1CO$ is a saturated aliphatic acyl radical containing 12 to 22 carbon atoms with magnesium oxide in a molar ratio of 1:0.5 to 1:1 at a reaction temperature in the range of from 320° to 345° C., wherein from 5 to 20% by weight of the total quantity of fatty acid is initially contacted with the magnesium oxide, the resulting mixture is heated to the reaction temperature, and the remaining fatty acid is added to the reaction mixture;

B) distilling off the fatty ketones as they are formed by the reaction from the reaction mixture under a reduced pressure of from 1 to 50 mbar; and C) reintroducing the bottom product accumulating during distillation step B) to the reaction mixture in a quantity approximately equal to the fatty acid consumed.

2. The process of claim 1 wherein in step A) in formula I $R^1CO$ is an acyl radical containing 16 to 18 carbon atoms.

3. The process of claim 2 wherein the acyl radical contains 18 carbon atoms.

4. The process of claim 1 wherein the molar ratio of fatty acid to magnesium oxide is from 1:0.6 to 1:1.

5. The process of claim 1 wherein in step A) the at least one fatty acid of formula I is a mixture of fatty acids obtained by the pressure hydrolysis of a fat or oil.

6. The process of claim 5 wherein the fat or oil is palm oil, palm kernel oil, coconut oil, rapeseed oil, sunflower oil, coriander oil, cotton oil, peanut oil, olive oil, linseed oil, soybean oil or beef tallow.

* * * * *